United States Patent [19]

de Korompay et al.

[11] Patent Number: 4,531,403
[45] Date of Patent: Jul. 30, 1985

[54] METHOD AND APPARATUS FOR FRACTURATION DETECTION

[76] Inventors: Susan A. de Korompay; Victor L. de Korompay, both of 119 Angell Ave., Beaconsfield, Quebec, Canada

[21] Appl. No.: 472,356

[22] Filed: Mar. 4, 1983

Related U.S. Application Data

[63] Continuation-in-part of Ser. No. 282,862, Jul. 13, 1981, abandoned.

[30] Foreign Application Priority Data

Aug. 1, 1980 [CA] Canada ................................. 357548

[51] Int. Cl.³ ...................... G01N 15/08; G01N 19/08
[52] U.S. Cl. ............................................ 73/38; 73/37; 73/40
[58] Field of Search .................. 73/37, 38, 40, 40.5 R, 73/46, 49.1, 49.5

[56] References Cited

U.S. PATENT DOCUMENTS

| 4,104,906 | 8/1978 | Oertle | 73/40 X |
| 4,135,386 | 1/1979 | Peterson et al. | 73/40 |
| 4,145,915 | 3/1979 | Oertle et al. | 73/37 |

FOREIGN PATENT DOCUMENTS

| 954053 | 11/1956 | Fed. Rep. of Germany | 73/38 |
| 181855 | 4/1966 | U.S.S.R. | 73/37 |
| 280951 | 9/1970 | U.S.S.R. | 73/38 |

Primary Examiner—Gerald Goldberg
Assistant Examiner—Joseph W. Roskos

[57] ABSTRACT

A method and apparatus for detecting cracks or other separations deep inside massive rock-like structures and assessing the integrity and safety of mine roofs and the like, wherein at least one borehole is drilled into the rock and a negative fluid pressure is applied thereto. The permeability of the rock at selected intervals along the borehole is measured and thereby the presence or absence of fractures in the rock is detected. The extension of the fracture to an adjoining hole may be determined by a pressure respond test in the adjoining hole.

18 Claims, 14 Drawing Figures

METHOD AND APPARATUS FOR FRACTURATION DETECTION

CROSS REFERENCE TO RELATED APPLICATIONS

This application is a continuation-in-part of our earlier filed U.S. patent application Ser. No. 282,862 filed July 13, 1981 and now abandoned.

FIELD OF INVENTION

This invention relates to a method and apparatus for detecting cracks in massive solid structures. More particularly this invention relates to methods and apparatus for detecting cracks, fractures or separated rock blocks in rock masses such as mine roofs and walls or in concrete structures or the like.

BACKGROUND OF THE INVENTION

Mine accident investigation statistics reveal that a surprisingly large number of fatal accidents occur every year through unpredictable roof falls, even in mines where all presently applicable safety regulations stipulated by the law are rigidly and meticulously enforced. Such accidents are routinely classified as "Act of God" because heretofore there has been no way for mining safety engineers to detect and monitor the development of dangerous, unstable rock conditions underground. Heretofore, the only methods to check the roof conditions have been (a) observation of the tensile strength increment on the rock bolts which indicates stress build-up in the roof and (b) "sounding" the rock by tapping it with a scaling bar. It will be appreciated, however, that neither of these methods is infallible because (a) tensile stress build-up may not occur because the rock bolts themselves may move with the sagging rock block and (b) the developed separations are initially very small and can be located very deeply within the rock mass so that tapping will fail to reveal any unsoundness.

BRIEF DESCRIPTION OF THE INVENTION

It is an object of the present invention to provide a simple and inexpensive method for detecting the presence of potentially dangerous cracks in massive structures such as the roof of an underground mine.

It is another object of the present invention to provide apparatus for use in the aforesaid method.

Thus, by one aspect of the invention there is provided a method for detecting fractures and determining the degree of fracturation in a rock mass or concrete of known matrix permeability having at least one borehole therein, comprising (a) pressure sealing a selected length of a selected borehole; (b) applying a negative fluid pressure to said borehole, and (c) measuring the fluid transmitting capacity of said rock through selected intervals along said borehole relative to matrix permeability.

By another aspect of this invention there is provided apparatus for detecting fractures and determining the degree of fracturation in a rock mass or concrete of known matrix permeability having at least one borehole therein, comprising:
(a) pressure sealing means to seal a selected interval along a borehole in a self-supporting rock mass;
(b) means to apply a negative fluid pressure to said sealed selected interval;
(c) means to measure fluid transporting capacity through said sealed selected interval relative to the matrix permeability of said rock mass.

DETAILED DESCRIPTION OF INVENTION

Figure 1A:
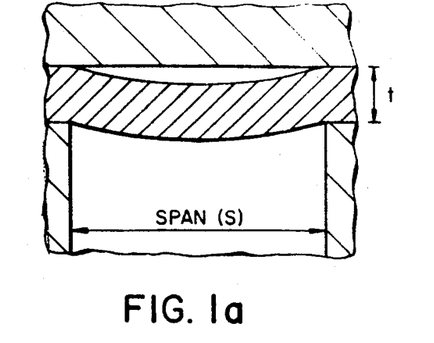
FIG. 1a, is a cross sectional view of a typical mine roof with a single bed.
Figure 1B:
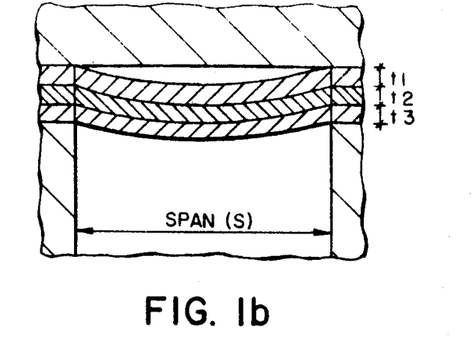
FIG. 1b, is a cross sectional view of a typical mine roof with multiple beds.

Rocks encountered in underground mining operations are generally considered to be heterogeneous because they contain, in varying degrees, geological fractures, fissures, joints, solution channels, cracks, faults and other mechanical discontinuities which create interfaces in the rock mass. Bond of tensile strength across these interfaces or partings can vary from zero to a value equal to or greater than the tensile strength of the host rock. During excavation of a stope, time-dependent deformations take place which tend to break fractures, joints and fault bonds creating instability in the roof. If the bond or tensile strength across the interface is very low the roof rock over the stope can become detached from the rock above to form a slab loaded only by its own weight (FIG. 1a) or additionally by thinner less rigid slabs above (FIG. 1b). This slab is known as the immediate roof and can be considered as a separate unit, the moments, shears and stresses of which can be calculated by beam theory.

Figure 2:
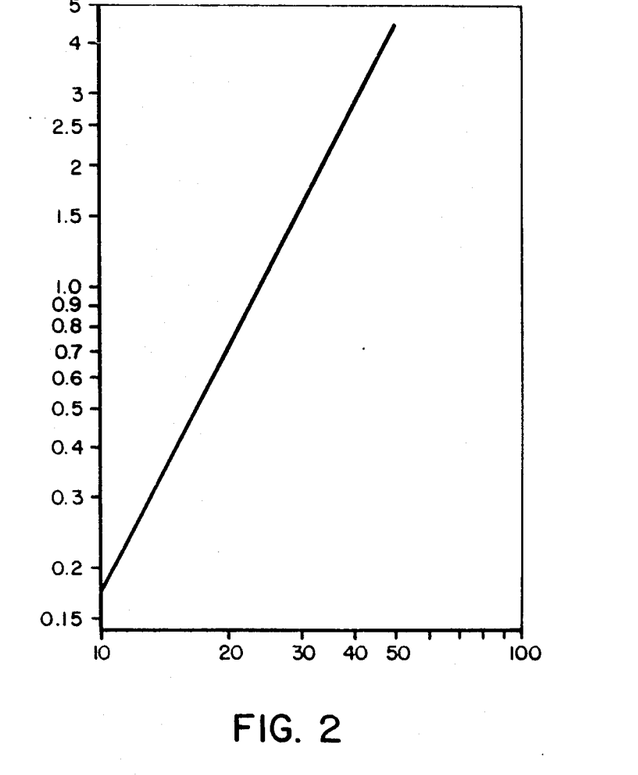
FIG. 2 is a graph illustrating the relationship between the thickness of a self-supporting beam and the span of a stope.

The equations for a horizontal roof single slab are:

$$T_{max} = \frac{3\gamma S}{4} \qquad 1$$

$$\sigma_{max} = \frac{\gamma S^2}{2t} \qquad 2$$

and the formula to calculate the thickness of a self-supporting beam is $$t = \frac{\gamma S^2}{2\sigma_{max}}$$

where
$T_{max}$ = maximum shear stress
$\theta max$ = maximum tensile stress
$\gamma$ = unit weight of rock
$S$ = span of stope
$t$ = thickness of immediate roof The relationship between the thickness of a self-supporting beam and the span of a stope is well known and is illustrated in graphical form in FIG. 2. It can be seen that, for a horizontal roof slab, a relatively thin immediate roof slab can be self-supporting and provided rock bolts are installed shortly after excavation, to secure the immediate roof to the main rock mass, the development of an immediately dangerous roof condition is very unlikely.

However, in the presence of joints and slip planes a completely separate rock block can be developed which is very weakly bonded to the main rock mass, and which is sometimes known as a "coffin roof" because of the dangers inherent therein. If the support under such a rock block is gradually removed by the mining operations, serious roof failure becomes imminent, depending on the orientation of the interfaces and the direction of stoping. Three different conditions can be developed in either a parallel or perpendicular plane relative to the direction of excavation:

(a) loose rock block supported at both ends;
(b) loose rock block supported at one end only; and
(c) loose rock block without support.

Figures 3A, 3B, 4A:
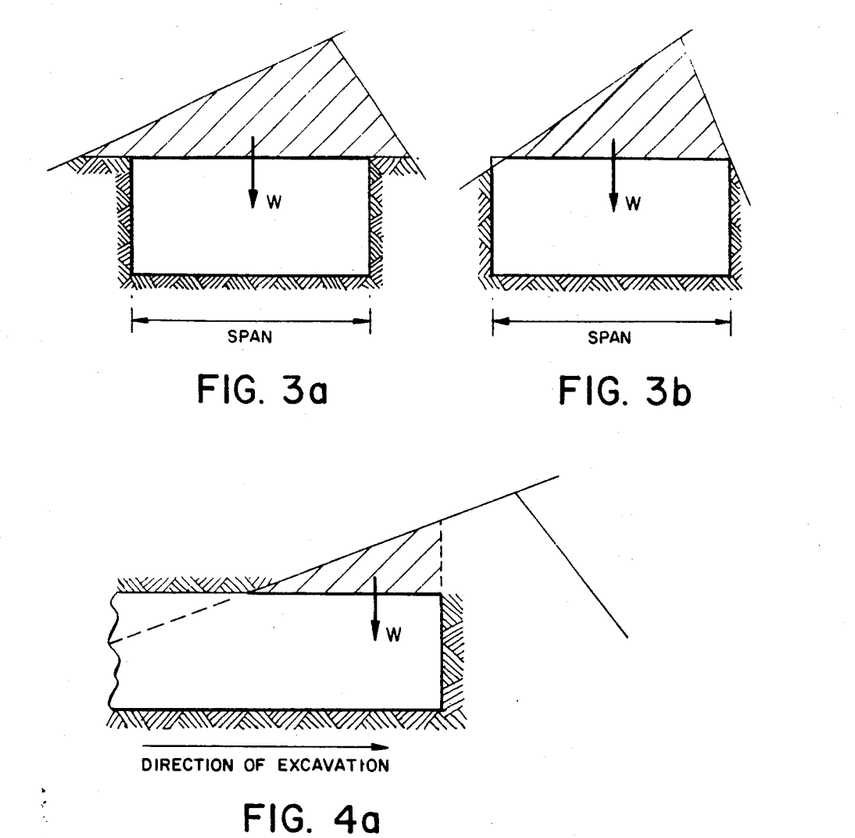
FIG. 3a is a cross section of a "coffin roof" with support in a mine, parallel to the stope.
FIG. 3b is a cross section of a "coffin roof" without support in a mine, parallel to the stope.
FIG. 4a is a cross section of a "coffin roof" with support in a mine, perpendicular to the stope.
Figure 4B:
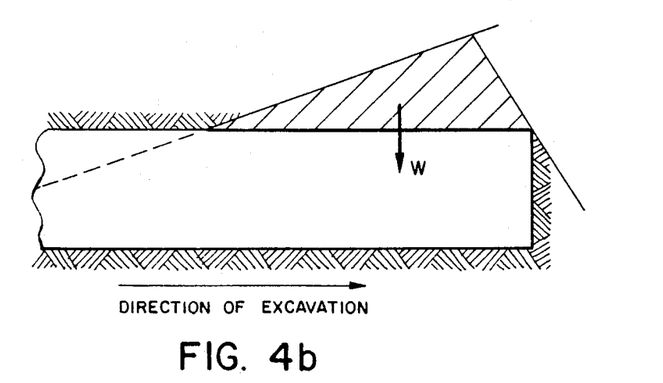
FIG. 4b is a cross section of a "coffin roof" without support in a mine, perpendicular to the stope.

The loose rock block in FIG. 3a is supported at both ends, acts as a self supporting beam clamped at both ends, and is inherently safe. If however the span of the stope is widened so that the planes of the interface tend toward intersection with the side walls of the stope, the support for the coffin roof is removed and it becomes unstable, as illustrated in FIG. 3b. Similarly the loose rock block shown in FIG. 4a acts as a gravity loaded cantilever beam and is inherently safe. FIG. 4b, however, illustrates what happens as the support is removed as the stope advances. The weight of the unsupported block gradually breaks the bond at the interface and roof collapse occurs.

Deterioration of a mine roof is generally a gradual process and actual collapse usually occurs several days or even weeks after initiation of the separation.

It is also known that the reduction of bond or tensile strength is always accompanied by the development of fine separations or cracks. Such cracks significantly increase the gas transmitting capacity of the rock mass.

Figure 6:
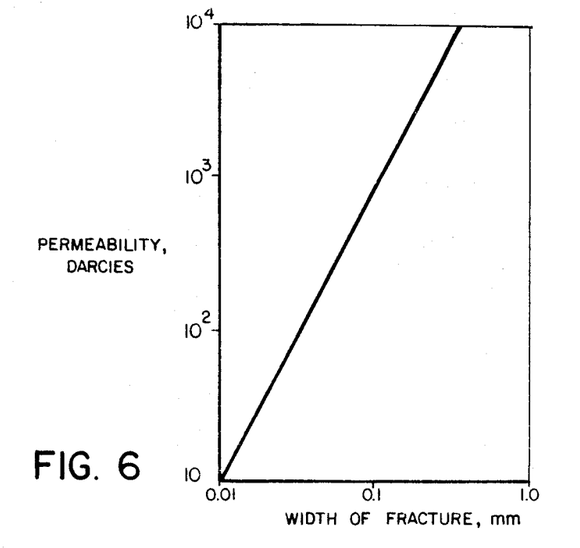
FIG. 6 is a graph illustrating fluid transmitting capabilities of fractured and solid rock.

Media that allow the passage of a fluid through them are said to be permeable. If the fluid movement takes place only in the naturally occurring pores and fractures and separation is absent, the permeability is referred to as "matrix permeability" and it is important to recognize that this represents permeability before fracturation. Absolute permeability expresses the fluid transmitting capacity of the medium when the pore space is 100 percent saturated with the fluid flowing in the medium. Absolute permeability of one darcy may be defined as that permeability which allows the flow of 1 cc per second of fluid of 1 centipoise viscosity through an area of 1 sq cm under a pressure gradient of 1 atm. per centimeter when the flow condition is viscous. It is known that the matrix permeability of unfractured rock normally encountered in underground mining operations is about 0.0001–0.001 darcies. As indicated in FIG. 6, however, rock with a 0.1 mm fracture through it, has a permeability of about 837 darcies, i.e. 800,000–8,000,000 times greater than the unfractured rock.

Figure 5:
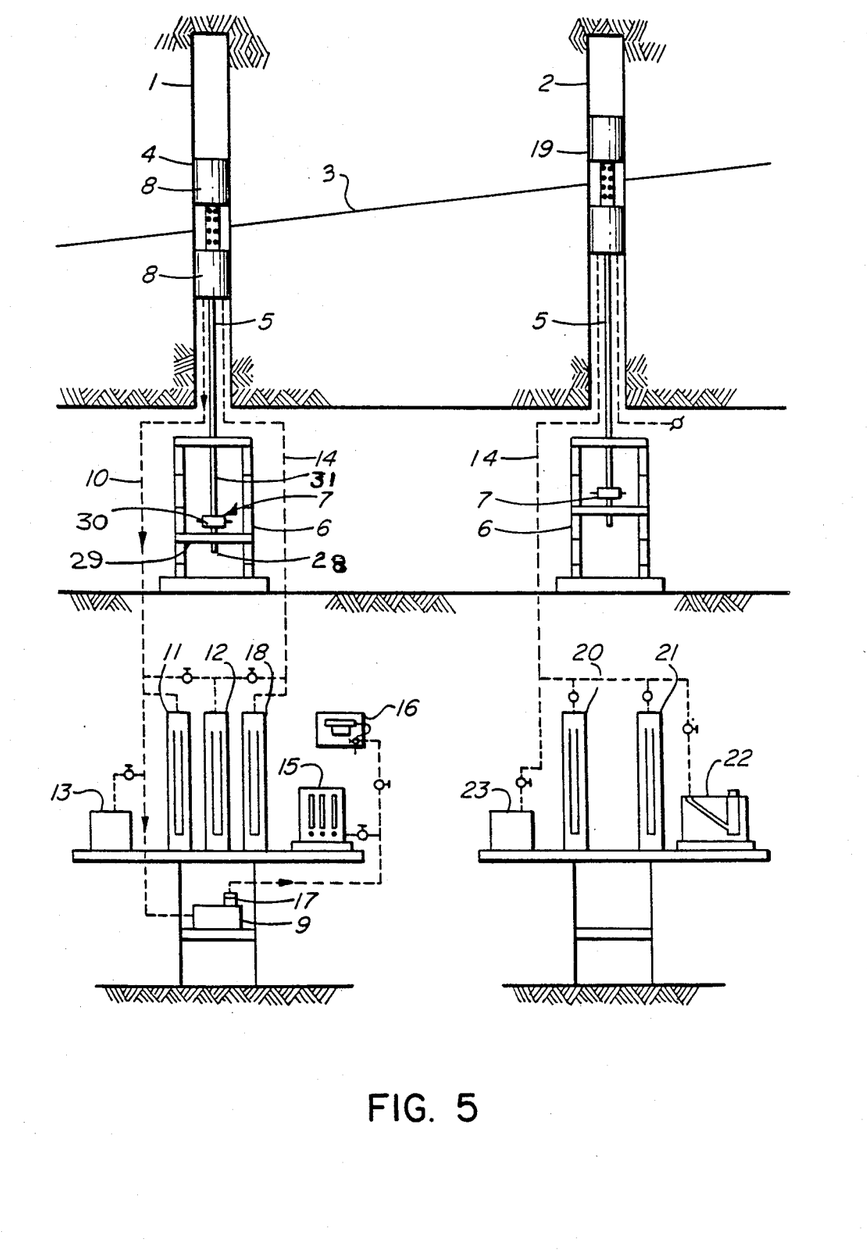
FIG. 5 is a schematic view in cross section of a mine roof showing the positioning and use of boreholes to determine fracturation according to the present invention.
Figure 8:
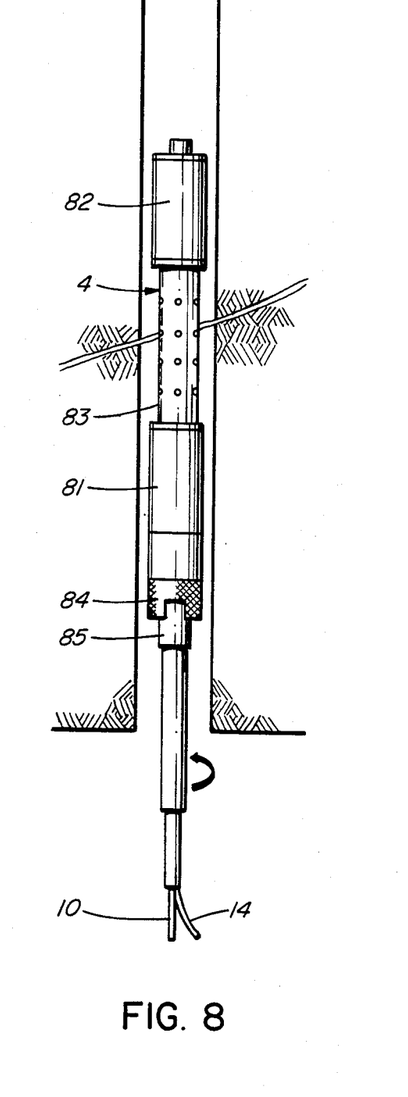
FIG. 8 is a sketch of a double or straddle packer of the present invention during installation.
Figure 9:
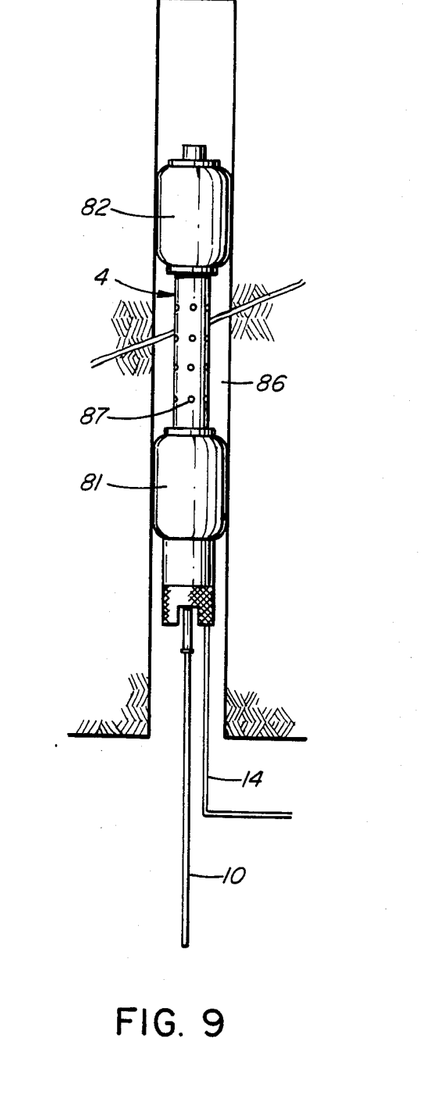
FIG. 9 is a sketch of the packer of FIG. 8 after installation.
Figure 10:
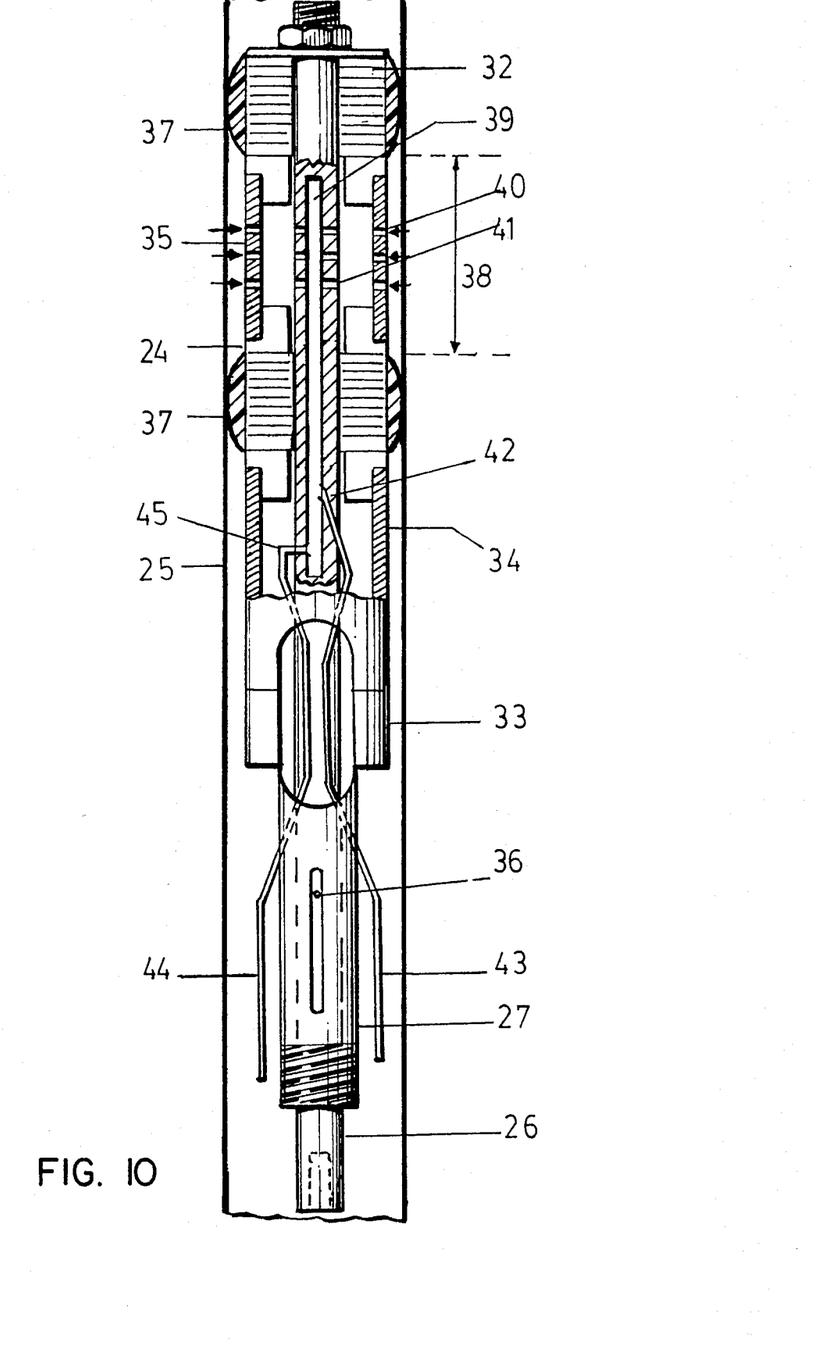
FIG. 10 is a cross sectional view of a dual flow line straddle packer.
Figure 11:
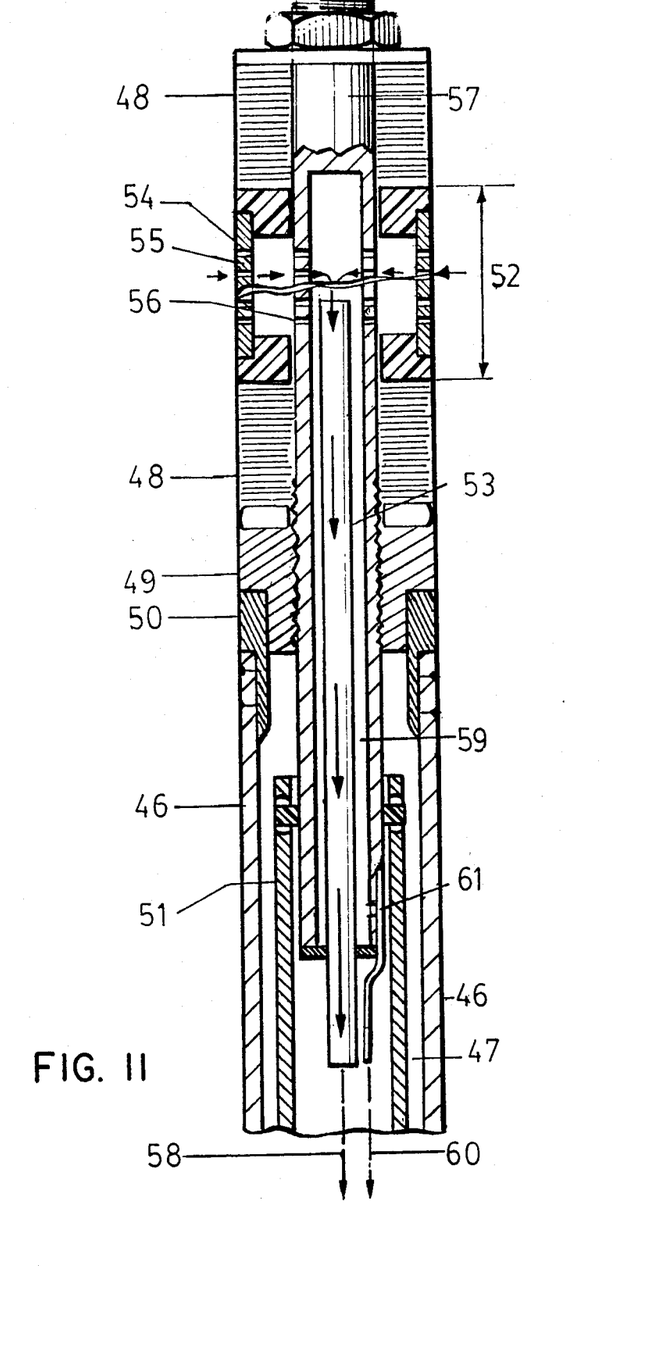
FIG. 11 is a cross section of a blast proof dual flow line straddle packer.

Rock/roof bolting is an accepted technique for reinforcing roofs in all types of rock. The function of the rock bolt is to bind together the stratified roof and suspend it by a bolt anchored in the self-supporting rock above it. Holes are drilled in the roof, at appropriate intervals, into the self-supporting rock mass and long steel bolts are inserted therein and anchored in the solid rock mass. A plate can then be secured to the free, lower end of the bolt and tensioned as desired to support the roof. It is convenient, therefore, that conventional rock bolt holes, 3–5 meters in length, be employed in the present invention according to which one hole is selected as the vacuum hole 1 while one or more other holes may be designated observation holes 2 (FIG. 5). A straddle packer 4 (described in more detail hereinafter) is inserted into vacuum hole 1 and a negative (vacuum) pressure is applied thereto by a vacuum pump 9 connected via line 10. It is of course well known that a fractured zone develops immediately adjacent the stope due to blasting and it is, therefore, important that the packer 4 should be installed beyond this zone so that the isolated zone is in a theoretically crack-free zone. The packer may be of the single or straddle variety. The single packer may be used to investigate the total length of a hole, but in order to locate and isolate a fracture at a particular position along the length of the hole, it is necessary to use a straddle packer which is also suitable for use in measuring the static, i.e. the "rock face" pressure directly FIGS. 8, 9, 10 and 11 illustrate a typical straddel packer suitable for the purposes of the present invention. A novel feature of the packer is that it uses dual flow lines to measure the dynamic and static i.e. the rock face pressure simultaneously with the flow rate measurement. The accurate rock face pressure measurement is the basic requirement for fracture evaluation. The packer assembly 24 is run in the test hole 25 by using the proper number of extension rods 26 and extension tubings 27. Setting tool 7 (in FIG. 5) or 85 (in FIG. 8) is used to set the packer at the selected location. The packer 24 is kept at the selected position by using the holder bolt 28 and plate 29 and stand 6 (in FIG. 5). By turning the setting wheel 30 and moving the setting pipe 31 upwards, rubber elements 32 are compressed by the forward movement of the extension tubings 27, crossover tubing connector 33, protector pipe 34 and spacer 35. Peg 36 prevents the turning of the extension tubing 27 during installation. After the deformation of the packers 37 (81, 82 in FIGS. 8 and 9) the investigation interval 38 (or 86 in FIG. 4) is completely isolated. Air flow is created by vacuum pump 9 (in FIG. 5). Air from investigated interval 38 enters into the hollow section of the base rod 39 through spacer 40 and base rod port holes 41 (87 in FIG. 9). Air is removed from the hollow section of the base rod 39 through flow line connection 42 and tubing flow line 43. The separate measuring line 44 is connected to the hollow section of the base rod 39 by the static line connection 45. The static line connection 45 is placed perpendicularly to the hollow section of the base rod 39 where no air movement takes place in order to measure the "rock face" pressure accurately. In order to release the packer it is necessary to turn the setting wheel 30 downward. It is mandatory to check the roof condition of the working face of a stope as close as possible where blasting is performed regularly. For this reason a packer which can not be damaged by blasting was developed. The packer uses dual flow lines to measure the dynamic and static i.e. the rock face pressure simultaneously with the flow rate (FIGS. 8, 9 and 11). The packer is placed at the selected section in the hole by using outside 46 and inside 47 extension pipes. The packer is set by compressing the rubber elements 48 by turning clockwise the coupling nut 49 with the turning head 50 fastened to the first outside extension pipe 46. During this operation the packer is held in position by the pipe holder 51 fastened to the first inside extension pipe 47 which prevents the turning of the packer. The deformation of the rubber elements 48 isolate the investigation interval 52 between the elements. After the installation of the packer, the outside 46 and inside 47 extension pipes with the turning head 50 and the pipe holder 51 are removed. The only exposed parts of the packer assembly are the tygon ® flow line 58 and the tygon ® static pressure measureing line 60. The air flow is induced by a vacuum pump. Air enters in the flow pipe 53 via spacer port holes 54 drilled in the spacer pipe 55 and base pipe port holes 56 drilled in the base pipe 57. The flow pipe 53 is connected to the vacuum pump by the tygon ® flow line 58. The static i.e. the rock face pressure, is measured in the annulus 59 where no air flow takes place. The annulus 59 is connected to the static manometer 18 (FIG. 1) via tygon ® static pressure measuring line 60 through port hole 61. The packer is released and removed from the hole by using the outside 46 and inside 47 extension pipes with turning head 50 and pipe holder 51. In this case the coupling nut 49 must be turned counterclockwise. As shown in FIG. 5, vacuum hole 1 and observation holes 2 drilled in the roof, intercepted a fracture 3. Straddle packer unit 4 is installed at various depths in the vacuum hole by using the extension rod assembly 5 and stand 6. The straddle packer 4 is set by turning the setting assembly 7 and isolate a section of the hole between the rubber elements 8. Then vacuum is created by the vacuum pump 9 through the flow line 10. The magnitude of the vacuum is measured by mercury manometer 11, water manometer 12 or vacuum gauge 13 by using static line 14. By moving the straddle packer in the hole and repeating the test the fracture 3 present in the rock mass is intercepted. In case of very small fractures (microfracture) the flow rate is very low and cannot be measured by commercially available flowmeters. In this case the flow rate is established by observing the absolute pressure change during unit time in a closed system which consists of the air volume between the rubber sealing elements of the packer, connection tubings, fittings manometer etc. The flow rate is calculated by using the following formula:

$$Q = \frac{(H_1 - H_2)}{760 t} \cdot \frac{520 \, V}{460 + T_f}$$

where:
Q—flow rate cc/min at 1 atm and 60° F. temp.
$H_1$, $H_2$—vacuum in Torr at the start and end of the observation period respectively
t—length of observation period—(minutes)
$T_f$—flowing air temperature (F.°) V—volume of closed system (cc).

To calculate the reservoir engineering parameters of the fracture the following formulas apply.

$$K = \frac{3.6 \, H_x}{P_e^2 - P_w^2}$$

$$T = \frac{0.82 \, K}{1000}$$

$$W_{mm} = \frac{\sqrt[3]{12 \cdot T}}{14.88}$$

where:
K=permeability (md)
T=transmissibility (darcy—feet)
$H_x$=pressure loss (Torr/min)
$P_e$, $P_w$=pressure at radius $r_e$ and $r_w$(psia)
$W_{mm}$=fracture size (mm)
h=investigation interval (25 cm)
d=packer diameter (1.5 in.)
v=vol. of closed system (500 cc).

In the case of larger fractures the flow rate may be measured by using area type flowmeter (rotameter) 15 or horizontal flowmeter 16 and flow line 10. By the application of the exhaust assembly 17 described in more detail hereinafter, the exhaust air is measured with the flowmeters at atmospheric condition instead of the flow rate under negative pressure. The prevailing negative pressure between the rubber elements (generally called "rock face pressure") which creates the air flow is measured by the mercury manometer 18 or water manometer 12 or vacuum gauge 13 by using the static line 14 in which no flow takes place. To calculate the reservoir engineering parameters of the fractures under these conditions, the following equations apply:

$$T = \frac{3.77 \, Q}{P_e^2 - P_w^2}$$

$$W_{mm} = \frac{\sqrt[3]{12 \cdot T}}{14.88}$$

$$K_f = 54 \times 10^6 \times W_{in}^2$$

where:
Kf=permeability (darcies)
T=transmissibility—(darcy-feet)
Q=flow rate (1/min)
$P_e$, $P_w$=pressure at radius $r_e$ and $r_w$ (psia)
$W_{mm}$=fracture size (mm)
$W_{in}$=fracture size (in.)
d=packer diameter (1.5 in.).

In order to establish the geological parameters i.e. strike, dip and areal extension of the fracture detected in hole 1, additional "observation holes" 2 may also be tested in conjunction with vacuum hole 1. A straddle packer 19 is inserted into each hole 2 in the same manner as in hole 1 and a test is conducted at selected intervals therealong until the fracture 3 intercepting hole 2 is isolated by straddle packer 19. The installation and setting the straddle packer in the observation hole 2 are identical with the procedure used in the vacuum hole 1. The continuity of a fracture between holes is established by observing the effect of the created vacuum in the vacuum hole 1 with the straddle packer 19 installed in the observation hole 2. The response is observed by mercury manometer 20 or water manometer 21, or inclined manometer 22, or vacuum gauge 23. A positive response indicates direct pneumatic connection between holes through the fracture. Pneumatic connection indicates that the tensile strength at the interface is zero. The utilization of a selected number of observation holes will determine the geometry of the loose rock block. After the determination of the geometry of the loose, separated rock block the stability of the underground opening is calculated by using beam theory as described hereinabove. Because roof deterioration is time dependent and gradual, repeated vacuum hole tests can be used to provide an early warning system to the mining engineer concerning an impending unstable roof condition. The vacuum method of the present invention is particularly suitable to monitor the deterioration of the fractured rock, because the air flow rate through a fracture increases by the cube of the width of the fracture. Unchanged pneumatic parameters indicate unchanged fracturation condition and vice versa. The formula to estimate the relative widening of the fracture by flow rate measurement using the original fracture width as unit is:

$$F = \frac{W_i}{W_o} = \sqrt[3]{\frac{Q_i}{Q_o}}$$

where:
F = fracture size ratio—(dimensionless)
$W_o$ = original fracture size (mm)
$W_i$ = increased fracture size (mm)
$Q_o$ = original flow rate at differential pressure P(cc/m)
$Q_i$ = increased flow rate at differential pressure P(cc/m).

It will, of course, be appreciated that when testing a mine roof for separation, application of a positive or hydrostatic pressure to observation hole 1 would impose an additional load on the rock which could be sufficient to cause roof collapse, and for this reason a vacuum or negative pressure is always applied to the observation hole when testing roofs. The invention is, however, equally applicable to the testing of side walls and the bottom or floor of the stope, and in these areas the application of a positive pressure does not impose such a safety hazard and under certain circumstances may be preferred. It will be appreciated that in certain applications, the integrity of roof, walls and floors is of considerable importance. For example, selection of a site for underground disposal of radioactive waste material, imposes a need to establish the sealing ability of the rock against migration of radionuclides in all directions. If samples of the gas flowing to the vacuum hole are taken for either in-situ analysis or analysis at a selected remote laboratory, it is possible to determine the presence or absence of possibly dangerous gases in the rock mass and/or radioactive material in the mass. Similarly fracturation problems in connection with concrete objects, such as foundations or dams may be investigated using either positive or negative pressure in the observation hole.

EXAMPLE

In order to illustrate the present invention, on a laboratory scale, a block of unfractured uranium ore, 100×100×100 cm thick was tested and found to have a matrix permeability of 0.005 md. A 70 cm Hg vacuum was drawn on one side of the block, while the other side of the block was at atmospheric pressure, and the time measured for this vacuum to decay to zero, i.e. equalization of pressure on both sides of the block. It was found that pressure equalization occurred in 180 minutes. After completion of this portion of the experiment a circular hole 0.34 mm in diameter was drilled through the sample to simulate fracturation. The vacuum pressure test was again applied and it was found that the 70 cm Hg vacuum equalized to atmospheric pressure in 2 minutes, indicative of a permeability of 3,6000,000 md. It will be observed the time index, i.e. ratio of the equalization time in unfractured rock to the equalization time in fractured rock = 180/2 = 90. It is obvious that such a drastic pneumatic condition change can be detected easily with very simple vacuum gauges.

The present invention is also useful to evaluate the best way of locating and arranging rock bolt installation in a mine roof. The basic requirement to install a rock bolt properly is to anchor it in a competent section of the rock mass overlying the underground opening. In this case the rock bolt suspends effectively the fractured rock below. But heretofore no method has been available to check the proper placement of the rock bolt anchor. The procedure to check the placement of the rock bolt with the vacuum method of the present invention is:

(1) determine the location of fractures present in the rock bolt holes prior to the installation of the rock bolt itself by using the method described hereinabove;
(2) based on the location of the fractures establish the thickness of the continuous roof section which can be considered as a beam; (H)
(3) calculate the thickness of the so-called self-supporting beam by using the formula:

$$h = \frac{\gamma S^2}{26}$$

where:
h = thickness of the self-supporting beam
$\phi$ = allowable tensile stress in the beam
$\gamma$ = unit weight of the rock
S = span of the opening;
(4) if the thickness of the continuous roof section (H) where the rock bolt anchor will be landed is larger than the thickness of the calculated self-supporting beam (h) the rock bolt installation is proper, i.e.:

H > h, if the h < H the rock bolt installation is not safe.

Figure 7:
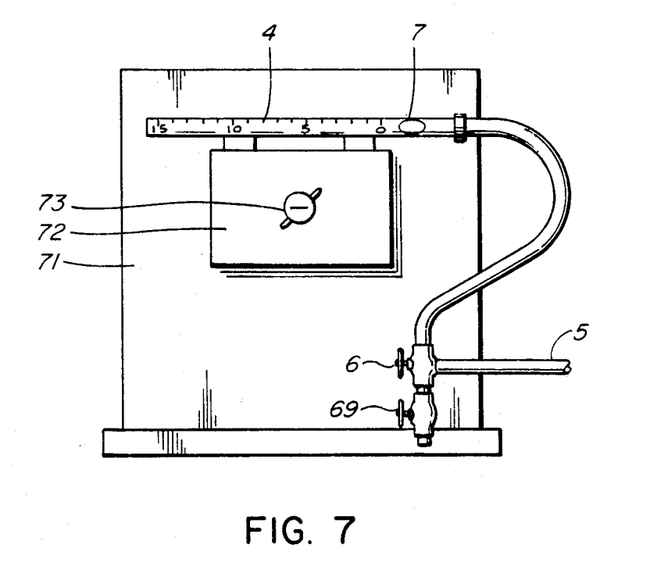
FIG. 7 is a sketch of a horizontal flow meter according to the present invention.

As noted hereinabove, fracture parameter determination in some cases requires measurement of flow rates which are far below the measuring range of commercially available rotameters or the like. It has, therefore, been necessary to develop a special flow meter capable of directly measuring air flow rates as low as 0.001 cc per minute or less. As shown in FIG. 7, a suitable flow meter 16 comprises a vertical frame 71 having a tube holder 72 pivotally mounted on a horizontal axis 73 thereon. A calibrated glass measuring tube 74 is mounted on holder 72 and connected to an air flow via plastic tubing 75 and normally open valve 76. Before making a measurement, valve 76 is closed to the formation and opened to atmosphere via valve 69 and a drop of water 77 is introduced, by a syringe, into tube 74 and positioned just beyond the zero mark by tilting tube 74 out of the horizontal. After placement the tube is restored to the horizontal position and valve 79 is closed while valve 76 is again opened. The flow rate is measured by recording the movement of the water drop along the tube, i.e., measuring the increase in volume during unit time. By using a water drop in a horizontal tube, rather than an air bubble in a vertical tube as in the well known bubblemeter, permits very low flow rates to be measured over measuring periods of the order of several days. At the low flow rates contemplated by the present invention, the specific weight of the flowing air can have a significant effect upon readings from a variable area type flow meter, and for this reason it is desirable to filter the exhaust air from the vacuum pump 9 (FIG. 5) before passing to horizontal flow meter 16, in order to eliminate oil mist from the air, through an exhaust assembly 17.

We claim:

1. A method for detecting fractures and determining the degree of fracturation in a rock mass or concrete of known matrix permeability having at least one borehole therein, comprising:
    (a) pressure sealing a selected length of a selected borehole;
    (b) applying a negative fluid pressure to said selected length of said selected borehole; and
    (c) measuring the fluid transmitting capacity of said rock mass through selected intervals along said borehole relative to matrix permeability.

2. A method as claimed in claim 1, wherein said negative pressure is applied at successive selected isolated intervals along the length of said borehole to thereby determine the longitudinal location of a fracture.

3. A method as claimed in claim 2 wherein the geometry of said fracture is determined by establishing successive selected isolated intervals in at least one additional borehole and measuring the pressure therein relative to the pressure in said selected borehole.

4. A method as claimed in claim 2 wherein said boreholes are located in at least one of roof, sidewalls and floor of a mine stope.

5. A method as claimed in claim 1, wherein said selected boreholes are rock bolt holes.

6. Apparatus for detecting fractures and determining the degree of fracturation in a rock mass or concrete of known matrix permeability having at least one borehole therein, comprising:
    (a) pressure sealing means to seal a selected interval along a borehole in a rock mass;
    (b) means to apply a negative fluid pressure to said sealed selected interval;
    (c) means to measure fluid transmitting capacity through said sealed selected interval relative to the matrix permeability of said rock mass.

7. Apparatus as claimed in claim 6 wherein said measuring means comprises flow rate metering means.

8. Apparatus as claimed in claim 6 wherein said measuring means comprises vacuum gauge means and timing means to determine rate of change of pressure.

9. Apparatus as claimed in claim 6 wherein said pressure sealing means comprises straddle packer means to thereby seal and isolate a selected interval of predetermined length along said borehole.

10. Apparatus as claimed in claim 9 including second straddle packer means for insertion into and sealing of a second selected borehole and means to measure pressure in said second selected borehole relative to pressure in said first borehole.

11. Apparatus as claimed in claim 10 including means to measure rock face pressure in the sealed selected interval of each of said first and second selected boreholes.

12. Apparatus as claimed in claim 6 wherein said means to measure fluid transmitting capacity includes a horizontal water bubble flow meter.

13. Apparatus as claimed in claim 6 including means to measure rock face pressure in said selected interval.

14. A method for monitoring deterioration of a roof in an underground mine stope comprising:
    (a) selecting at least one borehole in said roof;
    (b) pressure sealing a selected length of a selected borehole;
    (c) applying a negative fluid pressure to said selected sealed length of borehole; and
    (d) measuring rate of change of fluid flow rate through said selected sealed length over a selected period of time.

15. A method as claimed in claim 14 including determining relative rate of fracture widening wherein $$F = \frac{W_i}{W_o} = \sqrt[3]{\frac{Q_1}{Q_o}}$$

and wherein:
    F is fracture size ratio
    $W_o$ is original fracture size (mm)
    $W_1$ is increased fracture size (mm)
    $Q_o$ is original flow rate at differential pressure P
    $Q_1$ is increased flow rate at differential pressure P.

16. A straddle packer for use in detecting fractures and determining the degree of fracturation in a rock mass or concrete of known matrix permeability comprising
    (a) longitudinally extending mounting means;
    (b) a pair of expansile sealing means axially mounted in spaced relationship along said mounting means;
    (c) means to radially expand said sealing means in a borehole in said rock mass so as to provide an isolated gas space between said sealing means;
    (d) first fluid flowpath means between said gas space and vacuum pump means for creating fluid flow in said gas space; and
    (e) second fluid flowpath means between said gas space and pressure measuring means so as to determine static pressure in said gas space.

17. A straddle packer as claimed in claim 16 including screw means to expand said expansile sealing means.

18. A straddle packer as claimed in claim 16 including removable extension means for operating said screw means.

* * * * *